US00PP22188P2

(12) United States Plant Patent
Koning

(10) Patent No.: US PP22,188 P2
(45) Date of Patent: Oct. 4, 2011

(54) ***SENECIO* PLANT NAMED 'MOUNT EVEREST'**

(50) Latin Name: *Senecio ficoides*
Varietal Denomination: Mount Everest

(75) Inventor: Lammert Koning, Nuis (NL)

(73) Assignee: Koning & Koning B.V., Westerbrok (NL)

( * ) Notice: Subject to any disclaimer, the term of this patent is extended or adjusted under 35 U.S.C. 154(b) by 8 days.

(21) Appl. No.: 12/799,845

(22) Filed: May 4, 2010

(51) Int. Cl.
*A01H 5/00* (2006.01)

(52) U.S. Cl. ..... Plt./480

(58) Field of Classification Search ..... Plt./480
See application file for complete search history.

(56) References Cited

OTHER PUBLICATIONS

UPOV-ROM GTITM, Plant Variety Database, 2011/01, GTI Jouve Retrieval Software, Citation for plant 'Mount Everest'.*

* cited by examiner

*Primary Examiner* — Susan McCormick Ewoldt
(74) *Attorney, Agent, or Firm* — C. A. Whealy

(57) ABSTRACT

A new and distinct cultivar of *Senecio* plant named 'Mount Everest', characterized by its uniform, upright and mounded plant habit; upright, flat, broad and thick leaves; and blue green-colored leaves.

2 Drawing Sheets

Botanical designation: *Senecio ficoides*.
Cultivar denomination: 'MOUNT EVEREST'.

BACKGROUND OF THE INVENTION

The present invention relates to a new and distinct cultivar of *Senecio* plant, botanically known as *Senecio ficoides*, and hereinafter referred to by the name 'Mount Everest'.

The new *Senecio* plant is a product of a planned breeding program conducted by the Inventor in Paterswolde, The Netherlands. The objective of the breeding program was to develop new *Senecio* plants with unique and attractive leaf shape and plant form.

The new *Senecio* plant originated from a cross-pollination made by the Inventor in 2004 of a proprietary selection of *Senecio ficoides* identified as code name Portugal L52, not patented, as the female, or seed, parent with a proprietary selection of *Senecio ficoides* identified as code name Lin 05, not patented, as the male, or pollen, parent. The new *Senecio* plant was discovered and selected by the Inventor in 2006 as a single plant within the progeny of the stated cross-pollination in a controlled environment in Paterswolde, The Netherlands.

Asexual reproduction of the new *Senecio* plant by cuttings in a controlled environment in Paterswolde, The Netherlands since 2007 has shown that the unique features of this new *Senecio* plant are stable and reproduced true to type in successive generations.

SUMMARY OF THE INVENTION

Plants of the new *Senecio* have not been observed under all possible environmental conditions. The phenotype may vary somewhat with variations in environment such as temperature and light intensity, without, however, any variance in genotype.

The following traits have been repeatedly observed and are determined to be the unique characteristics of 'Mount Everest'. These characteristics in combination distinguish 'Mount Everest' as a new and distinct *Senecio* plant:

1. Uniform, upright and mounded plant habit.
2. Upright, flat, broad and thick leaves.
3. Blue green-colored leaves.

Plants of the new *Senecio* differ primarily from plants of the female parent selection in the following characteristics:

1. Plants of the new *Senecio* are upright whereas plants of the female parent selection are outwardly spreading.
2. Leaves of plants of the new *Senecio* are positioned around the stem whereas leaves of plants of the female parent selection are positioned on one side of the stem.

Plants of the new *Senecio* differ primarily from plants of the male parent selection in the following characteristics:

1. Plants of the new *Senecio* are more compact than and not as vigorous as plants of the male parent selection.
2. Leaves of plants of the new *Senecio* are positioned at a different angle than leaves of plants of the male parent selection.

Plants of the new *Senecio* can be compared to plants of *Senecio* 'Himalaya', not patented. In side-by-side comparisons conducted in Sappemeer, The Netherlands, plants of the new *Senecio* differed from plants of 'Himalaya' in the following characteristics:

1. Plants of the new *Senecio* were taller and more upright than plants of 'Himalaya'.
2. Lateral branches of plants of the new *Senecio* were longer and thicker than lateral branches of plants of 'Himalaya'.
3. Plants of the new *Senecio* had larger leaves than plants of 'Himalaya'.
4. Plants of the new *Senecio* and 'Himalaya' differed in leaf color as plants of 'Himalaya' had green-colored leaves.
5. Leaves of plants of the new *Senecio* were flat and broad whereas leaves of plants of 'Himalaya' were acicular.
6. Leaves of plants of the new *Senecio* were positioned more upright on the stems than leaves of plants of 'Himalaya'.

Plants of the new *Senecio* can also be compared to plants of *Senecio* 'Kilimanjaro', not patented. In side-by-side comparisons conducted in Sappemeer, The Netherlands, plants of the new *Senecio* differed from plants of 'Kilimanjaro' in the following characteristics:

1. Plants of the new *Senecio* were taller and more upright than plants of 'Kilimanjaro'.
2. Lateral branches of plants of the new *Senecio* were longer and thicker than lateral branches of plants of 'Kilimanjaro'.
3. Plants of the new *Senecio* had larger leaves than plants of 'Kilimanjaro'.
4. Leaves of plants of the new *Senecio* were flat and broad whereas leaves of plants of 'Kilimanjaro' were rounded.
5. Leaves of plants of the new *Senecio* were positioned more upright on the stems than leaves of plants of 'Kilimanjaro'.

BRIEF DESCRIPTION OF THE PHOTOGRAPHS

The accompanying photographs illustrate the overall appearance of the new *Senecio* plant. These photographs show the colors as true as it is reasonably possible to obtain in colored reproductions of this type. Colors in the photographs may differ slightly from the color values cited in the detailed botanical description which accurately describe the colors of the new *Senecio* plant.

The photograph on the first sheet comprises a side perspective view of a typical plant of 'Mount Everest' grown in a container.

The photograph on the second sheet is a close-up view of a typical plant of 'Mount Everest'.

DETAILED BOTANICAL DESCRIPTION

The aforementioned photographs, following observations and measurements describe plants grown in 12-cm containers during the summer in a glass-greenhouse in Sappemeer, The Netherlands and under conditions and practices which approximate those generally used in commercial *Senecio* production. During the production of the plants, day temperatures ranged from 18° C. to 25° C. and night temperatures ranged from 15° C. to 18° C. Plants were 13 weeks old when the photographs and description were taken. In the following description, color references are made to The Royal Horticultural Society Colour Chart, 2007 Edition, except where general terms of ordinary dictionary significance are used.

Botanical classification: *Senecio ficoides* 'Mount Everest'.

Parentage:

*Female, or seed, parent.*—Proprietary selection of *Senecio ficoides* identified as code name Portugal L52, not patented.

*Male, or pollen, parent.*—Proprietary selection of *Senecio ficoides* identified as code name Lin 05, not patented.

Propagation:

*Type.*—By cuttings.

*Time to initiate roots.*—About 20 days at soil temperatures of 18° C. to 20° C.

*Time to produce a rooted young plant.*—About 40 days at soil temperatures of 18° C. to 20° C.

*Root description.*—Fine, fibrous; light brown in color.

*Rooting habit.*—Freely branching; dense.

Plant description:

*Plant form/growth habit.*—Uniform, upright and mounded plant habit; moderately vigorous growth habit.

*Plant height.*—About 20.6 cm.

*Plant diameter.*—About 13.3 cm.

*Lateral branches.*—Length: About 10.5 cm. Diameter: About 1 cm. Internode length: About 5 mm. Strength: Moderately strong. Texture: Smooth, glabrous; waxy. Color: Between 147B and 191A; waxy bloom, close to 188B to 188C.

*Foliage description.*—Arrangement: Alternate, simple; sessile. Length: About 7 cm. Width: About 7 mm. Thickness: About 9 mm. Shape: Narrowly oblong to lanceolate, flat. Apex: Acute. Base: Cuneate. Margin: Entire. Texture, upper and lower surfaces: Smooth, glabrous; succulent; waxy. Venation pattern: Parallel. Color: Developing leaves, upper and lower surfaces: Close to 137C; waxy bloom, between 122B to 122C and 188A to 188B. Fully expanded leaves, upper and lower surfaces: Close to 137A to 137B; waxy bloom, between 122C and 188A to 188B; venation, close to 137A.

Flower description: Flower initiation and development have not been observed on plants of the new *Senecio*.

Disease/pest resistance: Plants of the new *Senecio* have not been observed to be resistant to pathogens and pests common to *Senecio*.

Temperature tolerance: Plants of the new *Senecio* have been observed to tolerate temperatures ranging from about 5° C. to about 35° C.

It is claimed:

1. A new and distinct *Senecio* plant named 'Mount Everest' as illustrated and described.

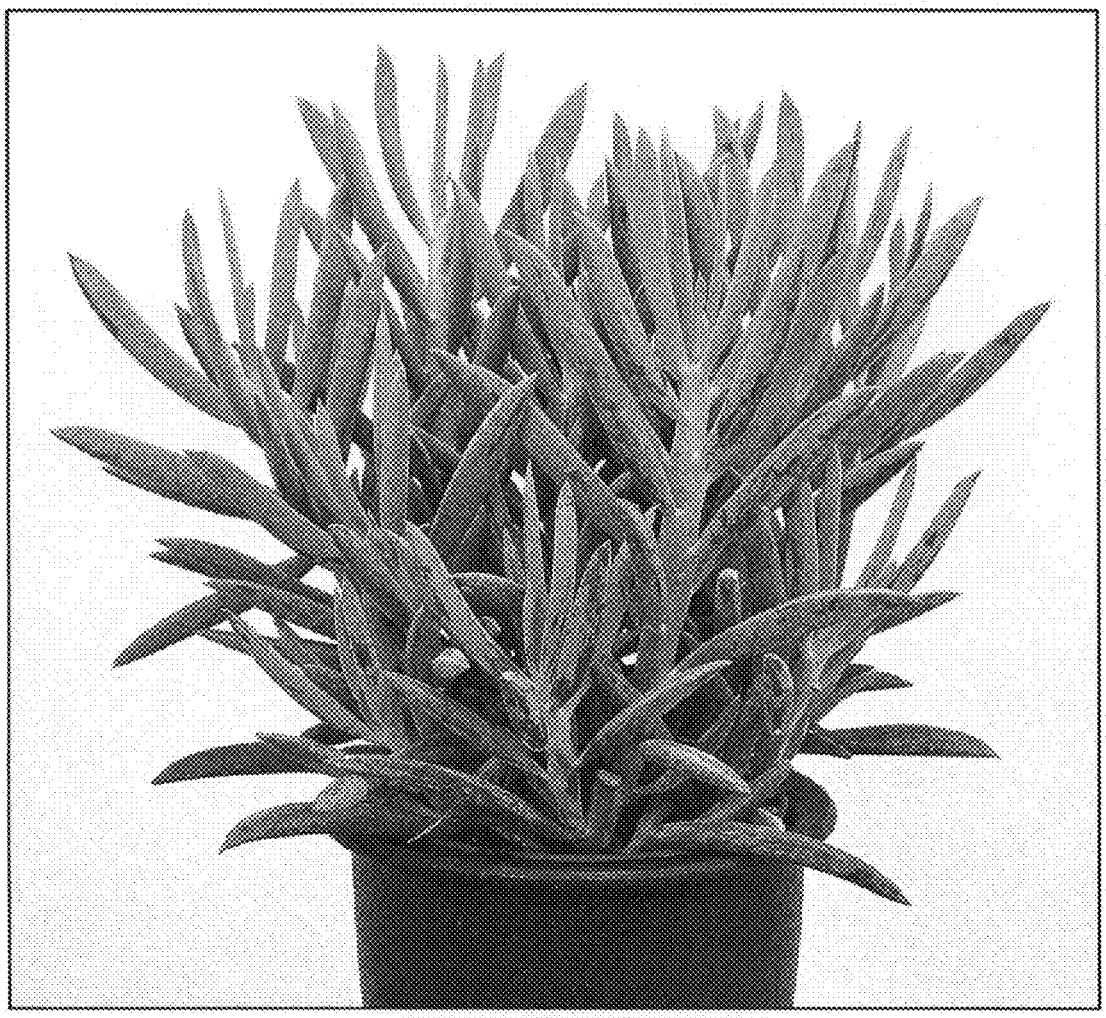

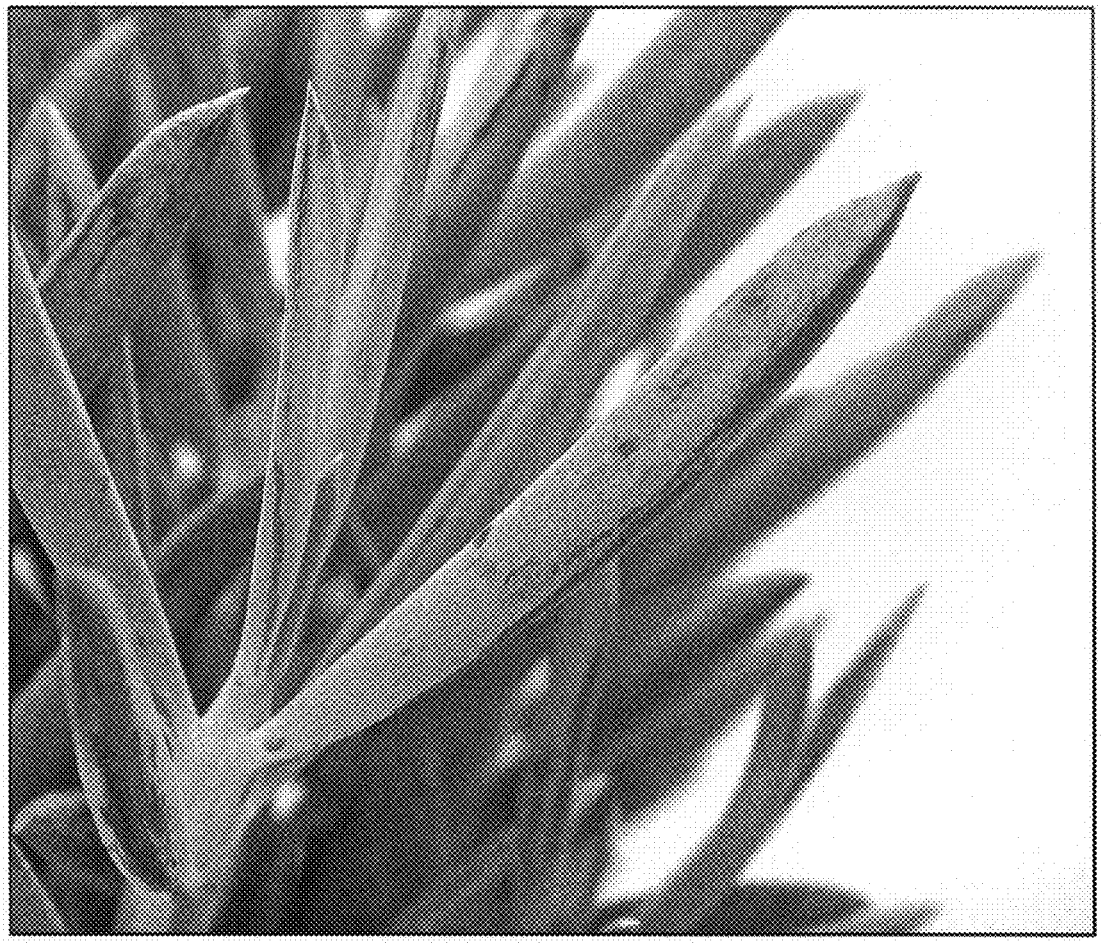

* * * * *